United States Patent [19]

Williams et al.

[11] Patent Number: 5,017,235
[45] Date of Patent: May 21, 1991

[54] SMOKING COMPOSITIONS CONTAINING A 2,5-DIACYLPYRAZINE FLAVORANT ADDITIVE

[75] Inventors: David L. Williams; Everett W. Southwick, both of Richmond, Va.

[73] Assignee: Philip Morris Inc., Richmond, Va.

[21] Appl. No.: 895,398

[22] Filed: Aug. 11, 1986

[51] Int. Cl.$^5$ .......................... A24B 3/12; A24B 15/38
[52] U.S. Cl. ..................................... 131/278; 131/276
[58] Field of Search ................................ 131/276, 278

[56] References Cited
U.S. PATENT DOCUMENTS
3,711,482 1/1973 Mookherjee et al. .

FOREIGN PATENT DOCUMENTS
0076085 4/1983 European Pat. Off. .
0119718 9/1984 European Pat. Off. .
2166323 11/1983 Fed. Rep. of Germany .

OTHER PUBLICATIONS
Journal of the Chemical Society, Perkin II, 1972, pp. 2035–2038.
Journal of Heterocyclic Chemistry, vol. 23, No. 2, Mar./Apr. 1987, pp. 497–500.
Bulletin of the Chemical Society of Japan, vol. 49, Oct. 1976, pp. 2805–2810.

Primary Examiner—V. Millin

[57] ABSTRACT

In one of its embodiments this invention provides smoking compositions which contain a novel unsymmetrical 2,5-diacylpyrazine flavorant additive as illustrated by 1-[5-(1-propanoyl)-2-pyrazinyl]-2-methyl-1-propanone:

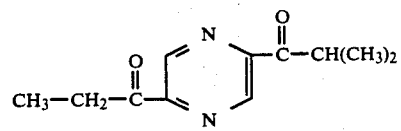

Under normal cigarette smoking conditions, the 2,5-diacylpyrazine additive volatilizes and enhances the flavor and aroma of the mainstream and sidestream smoke.

9 Claims, No Drawings

SMOKING COMPOSITIONS CONTAINING A 2,5-DIACYLPYRAZINE FLAVORANT ADDITIVE

BACKGROUND OF THE INVENTION

It has been established that alkylpyrazines are natural components of tobacco smoke, and that they most probably are important contributors to tobacco smoke flavor [A. Baggett et al; J. Chromatog. 97, 79 (1974)]. Further, it has been disclosed in the patent literature that addition of alkylpyrazines to tobacco results in an improvement in the flavor of smoking compositions as judged by an expert panel under subjective test conditions.

U.S. Pat. No. 3,402,051 describes a process for imparting a popcorn-like flavor and aroma to tobacco and foodstuffs by the incorporation of a 2-acetylpyrazine derivative therein.

Other patents which disclose the addition of various pyrazine compounds to tobacco and foodstuffs as a means of providing flavor or flavor enhancement include U.S. Pat. Nos. 3,684,809; 3,705,158; 3,754,934; 3,764,349; 3,767,426; and 3,881,025.

U.S. Pat. No. 3,914,227 discloses pyridyl and pyrazyl ketones and their use in altering the organoleptic properties of tobacco and foodstuffs, and U.S. Pat. No. 4,166,869 discloses acylpyrimidines useful as flavorants for the same type of applications.

Alkylpyridines have also been found to be useful tobacco additives. As an example, U.S. Pat. No. 3,625,224 describes the use of methylpyridines, ethylpyridines and various dialkylpyridines as tobacco additives. U.S. Pat. No. 3,381,691 discloses 2-methyl-5-isopropylpyridine as a tobacco additive.

It is characteristic of pyridine, pyrazine, pyrimidine and other heterocyclic derivatives employed as tobacco flavorants in the prior art, as illustrated by the above described technical literature, that the respective heterocyclic derivatives have the disadvantage of both high volatility and low odor threshold. Both of these properties significantly restrict the extent that these heterocyclic derivatives can be utilized as flavorants in tobacco compositions. A quantity of a pyrazine or pyridine derivative in a tobacco composition sufficient to have a noticeable effect in low delivery cigarettes causes a marked pack aroma.

U.S. Pat. No. 4,259,969 endeavors to overcome some of the disadvantages of the above recited flavorant technology. The said patent describes smoking composition flavorant-release additives such as 2,3-dihydroxy-2,3-dimethyl-1,4-bis(3,5,6-trimethyl-2-pyrazinyl)butane. Under smoking conditions there are released substituted-pyrazine pyrolysis products which enhance the flavor of the mainstream smoke and improve the aroma of the sidestream smoke.

There is continuing research effort to develop improved smoking compositions which contain a new and efficient low volatility flavorant additive, and which generate mainstream smoke with flavorant-enhanced taste and character under smoking conditions.

Accordingly, it is an object of this invention to provide smoking compositions having incorporated therein a flavorant component which is characterized by lack of mobility and/or volatility at ambient temperature.

It is another object of this invention to provide smoking compositions having incorporated therein an additive which under normal smoking conditions contributes improved flavor to mainstream smoke and improved aroma to sidestream smoke.

It is a further object of this invention to provide a novel class of unsymmetrical 2,5-diacylpyrazine compounds.

Other objects and advantages of the present invention shall become apparent from the following description and examples.

Other literature of background interest with respect to the present invention are U.S. Pat. No. 3,452,014 and U.S. Pat. No. 4,064,124 which describe the synthesis of 2,5-disubstituted and 2,3,5,6-tetrasubstituted pyrazines which have utility as starting materials for the manufacture of dyes, fungicides and pharmaceuticals.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001–5 weight percent, based on the total weight of filler, of a 2,5-diacylpyrazine additive corresponding to the formula:

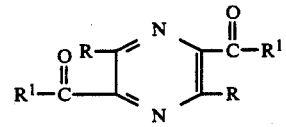

where R is hydrogen or an alkyl radical containing between about 1-4 carbon atoms; and $R^1$ is an alkyl radical containing between about 1-10 carbon atoms.

Illustrative of the R substituent are hydrogen, methyl, ethyl, propyl, butyl, isobutyl and 2-butyl radicals.

Illustrative of the $R^1$ substitutent are methyl, ethyl, butyl, pentyl, isopentyl, hexyl, heptyl, octyl and decyl radicals.

In another embodiment, this invention provides a smoking composition comprising an admixture of (1) combustible filler selected from natural tobacco, reconstituted tobacco and tobacco substitutes, and (2) between about 0.0001–5 weight percent, based on the total weight of filler, of an unsymmetrical 2,5-diacylpyrazine additive corresponding to the formula:

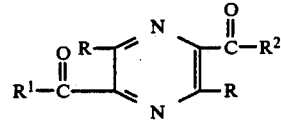

where R is hydrogen or an alkyl radical containing between about 1-4 carbon atoms; and $R^1$ and $R^2$ are alkyl radicals containing between about 1-10 carbon atoms, and $R^1$ and $R^2$ are different alkyl groups.

R is hydrogen and $C_{1-4}$ alkyl radicals as previously illustrated. $R^1$ and $R^2$ are $C_{1-10}$ alkyl radicals as previously illustrated.

Preparation Of 2,5-Diacylpyrazines

A general procedure for the preparation of a present invention unsymmetric 2,5-diacylpyrazine derivative involves the reaction of a selected pyrazine compound with an alkanal in a two phase aqueous-organic solvent medium:

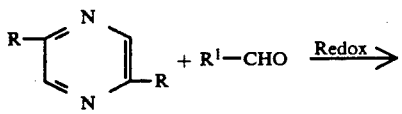 (1)

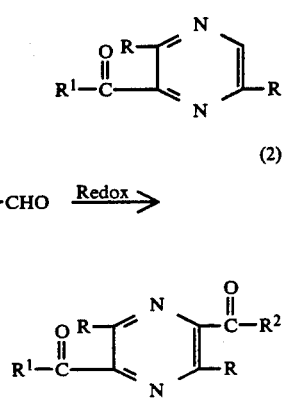 (2)

Symmetrical 2,5-diacylpyrazine compounds are known, and can be prepared as illustrated in Example VI using the Caronna et al procedure described in J. Chem. Soc., Perkin Trans. 2, 14, 2035 (1972). In the Example VI procedure, a homogeneous reaction medium favors the formation of a symmetrical 2,5-diacylpyrazine, rather than a monoacylpyrazine as in step (1) of the above flow diagram.

Symmetrical 2,5-diacylpyrazines also are reported in other technical literature such as Bull. Chem. Soc. Japan, 49(10), 2805 (1976) by K. Yamada et al.

The present invention 2,5-diacylpyrazines are stable and odorless compounds at ambient temperature. An invention 2,5-diacylpyrazine compound, when incorporated in a smoking composition, is a low volatility additive which under normal smoking conditions volatilizes and enhances the flavor and aroma of low delivery cigarette smoke, as demonstrated in Example VII.

Preparation Of Smoking Compositions

In a further embodiment, this invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001–5 weight percent, based on composition weight, of a 2,5-diacylpyrazine additive corresponding to the formula:

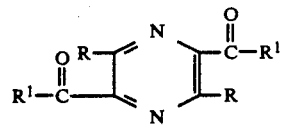

where R is hydrogen or an alkyl radical containing between about 1–4 carbon atoms; and $R^1$ is an alkyl radical containing between about 1–10 carbon atoms.

The invention 2,5-diacylpyrazine flavorant additive can be incorporated into the tobacco or tobacco substitute in accordance with methods known and used in the art. Preferably the flavorant additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant additive may be incorporated as part of a concentrated tobacco extract which is applied to a fibrous tobacco web as in the manufacture of reconstituted tobacco. Another suitable procedure is to incorporate the flavorant additive in tobacco or tobacco substitute filler in a concentration between about 0.5–5 weight percent, based on the weight of filler, and then subsequently to blend the treated filler with filler which does not contain flavorant additive.

The term "tobacco substitute" is meant to include non-tobacco smoking filler materials such as are disclosed in U.S. Pat. Nos. 3,703,177; 3,796,222; 4,019,521; 4,079,742; and references cited therein; incorporated herein by reference.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

The following Examples are further illustrative of the present invention. The specific ingredients and processing parameters are presented as being typical, and various modifications can be derived in view of the foregoing disclosure within the scope of the invention.

EXAMPLE I 1-(2,5-Dimethyl-3-pyrazinyl)-1-propanone

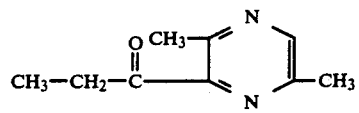

To a stirring heterogeneous mixture of 2,5-dimethylpyrazine (10.8 g, 100 mmoles), freshly distilled propionaldehyde (35 g, 600 mmoles), 3.4M sulfuric acid (50 ml) and benzene (200 ml) cooled in an ice bath (5° C.) is added concurrently a solution of ferrous sulfate heptahydrate (168 g, 600 mmoles) in water (400 ml) and 70% t-butylhydroperoxide (54 g, 420 mmoles) over a 15–20 minute period. The resulting mixture is stirred at 5° C. for 2 hours and then allowed to stand at room temperature for 64 hours.

The benzene layer is separated, dried (magnesium sulfate) and stripped to give 22.1 g of a residual crude mixture. The crude mixture is dissolved in diethyl ether (250 ml) and washed with water (250 ml) and saturated aqueous sodium bicarbonate (200 ml). The ethereal layer is dried (MgSO$_4$) and stripped to give 12.5 g of crude product.

Volatile impurities are removed from the crude product by employing aspirator pressure and a low temperature (b.p. 45° C./30 mm Hg). Vacuum pump distillation provides high purity 1-(2,5-dimethyl-3-pyrazinyl)-1-propanone as a low melting solid (3.8 g, 23% yield).

An analytically pure sample is obtained by preparative GLC; and IR, NMR and MS data confirm the structure.

Anal. Calc. for $C_9H_{12}N_2O$: C, 65.83; H, 7.37; N, 17.06. Found: C, 65.63; H, 7.48; N, 17.23.

EXAMPLE II

1-[3,6-Dimethyl-5-(1-propanoyl)-2-pyrazinyl]-3-methyl-1-butanone

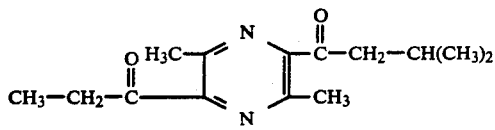

To a cold (0° C.) solution of 2,5-dimethyl-3-propionylpyrazine (1.64 g, 10 mmoles) in glacial acetic acid (15 ml) is added concentrated sulfuric acid (3 ml), water (15 ml) and isovaleraldehyde (4.3 g, 50 mmoles). A solution of ferrous sulfate heptahydrate (5.56 g, 20 mmoles) in water (10 ml) is then added, followed by 70% t-butylhydroperoxide (2.6 g, 20 mmoles). The resulting dark brown solution is stirred for 2 hours at 0° C., and GLC analysis (5% carbowax-20M; 120°-220° C., 10°/min; ⅛"×10') indicates the absence of starting material.

The reaction medium is poured into water (150 ml), and the aqueous mixture is extracted with methylene chloride (3×25 ml). The combined organic extracts are washed with water (150 ml), and with saturated aqueous sodium bicarbonate (150 ml), and then dried ($MgSO_4$). The solvent is removed under reduced pressure to give 2.25 g of a crude oil.

Silica gel chromatographic elution with 25% methylene chloride in hexane provides pure 1-[3,6-dimethyl-5-(1-propanoyl)-2-pyrazinyl]-3-methyl-1-butanone (1.15 g, 47% yield).

IR, NMR and MS data confirm the structure.

Anal. Calc. for $C_{14}H_{20}N_2O_2$: C, 67.72; H, 8.12; N, 11.28. Found: C, 67.87; H, 8.33; N, 11.45.

EXAMPLE III

1-[5-(1-Ethanoyl)-2-pyrazinyl]-2,2-dimethyl-1-propanone

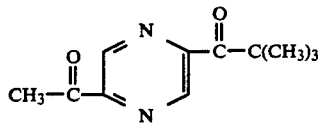

To a cold (5°-10° C.) solution of acetylpyrazine (7.1 g, 58 mmoles) in glacial acetic acid (87 ml) is added concentrated sulfuric acid (17.4 ml), water (87 ml), and trimethylacetaldehyde (25 g, 290 mmoles). A solution of ferrous sulfate heptahydrate (32.3 g, 116 mmoles) in water (58 ml) is then added followed by 70% t-butylhydroperoxide (14.9 g, 116 mmoles). The resulting dark brown solution is stirred for 1 hour with the temperature rising to 20° C., and GLC analysis (5% Carbowax-20M; 190° C.; ⅛"×10') indicates no starting material.

The resulting reaction product mixture is quenched with solid sodium sulfite until test with starch-iodide paper is negative, and then extracted with diethyl ether (3×200 ml). The combined organic layers are washed with saturated aqueous sodium bicarbonate (3×100 ml), and with saturated aqueous sodium chloride, and then dried ($MgSO_4$).

The solvent is removed under reduced pressure to give 11.5 g of a crude brown oil. Silica gel (200 g of silica gel 60) chromatographic elution with 3% ethyl acetate/hexane provides high purity 1-[5-(1-ethanoyl)-2-pyrazinyl]-2,2-dimethyl-1-propanone [5.0 g, 42% yield (m.p. 41°-42.5° C.)].

An analytically pure sample is obtained by preparative GLC; and IR, NMR and MS spectra confirm the structure.

Anal. Calc. for $C_{11}H_{14}N_2O_2$: C, 64.06; H, 6.84; N, 13.58. Found: C, 64.16; H, 6.96; N, 13.64.

EXAMPLE IV 1-(2-Pyrazinyl)-1-propanone

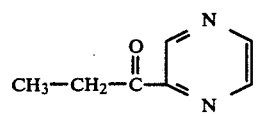

To a stirring heterogeneous mixture of pyrazine (800 mg, 10 mmoles), freshly distilled propionaldehyde (3.48 g, 60 mmoles) and 3.4M sulfuric acid (5 ml) cooled in an ice bath (3° C.) is added concurrently a solution of ferrous sulfate heptahydrate (16.7 g, 60 mmoles) in water (40 ml) and 70% t-butylhydroperoxide (5.4 g, 42 mmoles) over a 10 minute period. The resulting mixture is stirred for 1 hour with the temperature rising to 15° C.

The reaction mixture is quenched with solid sodium sulfite until test with starch-iodide paper is negative, and then extracted with methylene chloride (3×40 ml). The combined organic layers are washed with saturated aqueous sodium bicarbonate (1×40 ml), with saturated aqueous sodium chloride (1×40 ml), and then dried ($MgSO_4$). The solvent is removed under reduced pressure to give 2.3 g of a crude brown oil.

Flash distillation (25° C. at 1 mm Hg) removed the volatile impurities, and a second fraction (50° C. at 1 mm Hg) containing the product is isolated. The latter fraction is sublimed (55° C. at 1 mm Hg) to provide a 29% yield (390 mg, 2.87 mmoles) of 1-(2-pyrazinyl)-1-propanone (m.p. 46°-47° C.).

An analytically pure sample is obtained by preparative GLC; and IR, NMR and MS spectra confirm the structure.

Anal. Calc. for $C_7H_8N_2O$: C, 61.75; H, 5.93; N, 20.58. Found: C, 61.55; H, 5.81; N, 20.41.

EXAMPLE V

1-[5-(1-Propanoyl)-2-pyrazinyl]-2-methyl-1-propanone

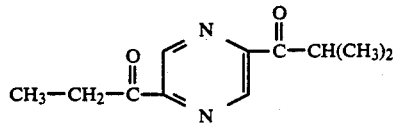

To a stirring heterogeneous mixture of 2-propionylpyrazine (1.0 g, 7.35 mmoles), freshly distilled isobutyraldehyde (3.2 g, 44 mmoles) and 3.4M sulfuric acid (3.7 ml) cooled in an ice bath (10° C.) is added concurrently a solution of ferrous sulfate heptahydrate (12.2 g, 44 mmoles) in water (30 ml) and 70% t-butylhydroperoxide (4.0 g, 31 mmoles) over a 10 minute period. After stirring the dark solution for 15 minutes at 15° C., hexane (30 ml) is added and the resulting mixture stirred an additional 45 minutes. The mixture is quenched with solid sodium sulfite until test with starch-iodide paper is negative, and then extracted with hexane (3×30 ml). The combined organic layers are washed with water (30 ml), with saturated sodium bicarbonate (2×30 ml), and with saturated aqueous sodium chloride (30 ml).

After drying (MgSO$_4$), the solvent is removed under reduced pressure to give 1.5 g of a crude red-brown oil. Purification via circular preparative chromatographic (Chromatotron coated with silica gel GF-254) elution with 2% ethyl acetate/hexane provides a 43% yield of high purity 1-[5-(1-propanoyl)-2-pyrazinyl]-2-methylpropanone (650 mg, 3.16 mmoles).

Crystallization from hot hexane produces yellow needles of 1-[5-(1-propanoyl)-2-pyrazinyl]-2-methyl-1-propanone (m.p. 70°-71° C.). IR, NMR and MS spectra confirm the structure.

Anal. Calc. for C$_{11}$H$_{14}$N$_2$O$_2$: C, 64.06; H, 6.84; N, 13.58. Found: C, 64.17; H, 6.94; N, 13.88.

EXAMPLE VI

Preparation of 1,1'-(2,5-Pyrazinediyl)bis-1-propanone

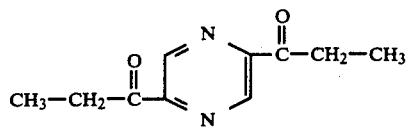

The reaction of pyrazine and propionaldehyde is conducted on a 10 mmole scale using the Caronna et al procedure described in *J. Chem. Soc., Perkin Trans.* 2, 14, 2035-8 (1972). A 50% crude yield of 1,1'-(2,5-pyrazinediyl)bis-1-propanone is obtained.

Crystallization from hexane produces yellow needles of analytically pure quality (M.P. 112°-112.5° C.). IR, NMR and MS data confirm the structure.

Anal. Calc. for C$_{10}$H$_{12}$N$_2$O$_2$: C, 62.48; H, 6.29; N, 14.58. Found: C, 62.75; H, 6.23; N, 14.81.

EXAMPLE VII

Preparation Of Smoking Compositions Containing An Invention 2,5-Diacylpyrazine Additive Cigarettes are fabricated employing a blend of tobaccos treated with an ethanolic solution of an invention 2,5-diacylpyrazine additive to provide 50-400 ppm of the compound by weight of the tobacco. The cigarettes are targeted to deliver 8 mg of tar per cigarette.

Untreated controls are prepared and the treated cigarettes are compared to the controls by an experienced smoking panel. The treated cigarettes are found to have the subjective test flavorant properties listed in the Table, as compared to the controls.

The subjective properties of the invention 2,5-diacylpyrazine flavorants generally are judged to be different from the popcorn-like flavorant properties of 2-acetylpyrazine disclosed in U.S. Pat. No. 3,402,051, the potato-like flavorant properties of 2-acetyl-3-ethylpyrazine disclosed in U.S. Pat. No. 3,767,428, and the sweet chocolate flavorant properties of 1-[5-(2-methyl-1-propyl)-2-pyrazinyl]-1-propanone disclosed in copending patent application Ser. No. 467,412 (filed Feb. 17, 1983).

TABLE

| Example | Structure | PPM | Subjective Flavorant Properties |
|---|---|---|---|
| II | CH$_3$—CH$_2$—C(O)—[pyrazine with OCH$_3$, CH$_3$]—C(O)—CH$_2$—CH(CH$_3$)$_2$ | 50 | green leafy side stream aroma; interesting burley tobacco notes, but not barnyard-like; lightly salty; slight metallic aftertaste. |
| III | CH$_3$—C(O)—[pyrazine]—C(O)—C(CH$_3$)$_3$ | 400 | sweet, smoother, cocoa-chocolate flavor; oily coating; more body with increased tobacco taste. |
| V | CH$_3$—CH$_2$—C(O)—[pyrazine]—C(O)—CH(CH$_3$)$_2$ | 300 | roasted; nutty; flue-cured; sweet, enhanced with low green bitter, smooth and blended flavor. |
| VI | CH$_3$—CH$_2$—C(O)—[pyrazine]—C(O)—CH$_2$—CH$_3$ | 300 | increased sweet, smoother flavor, with green-bitter character. |

TABLE-continued

| Example | | PPM | Subjective Flavorant Properties |
|---|---|---|---|
| (a) | 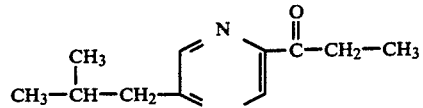 | 70-100 | sweet chocolate flavor. |

(a) Disclosed in copending patent application S.N. 467,412.

What is claimed is:

1. A smoking composition comprising an admixture of (1) combustible filler selected from natural tobacco, reconstituted tobacco and tobacco substitutes, and (2) between about 0.0001-5 weight percent, based on the total weight of filler, of a 2,5-diacylpyrazine additive corresponding to the formula:

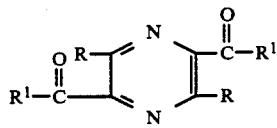

where R is hydrogen or an alkyl radical containing between about 1-4 carbon atoms; and $R^1$ is an alkyl radical containing between about 1-10 carbon atoms.

2. A smoking composition in accordance with claim 1 wherein the non-tobacco substitutes are selected from pectinaceous, cellulosic and carbohydrate materials.

3. A smoking composition in accordance with claim 1 wherein the two $R^1$ alkyl radicals are the same.

4. A smoking composition in accordance with claim 1 wherein the 2,5-diacylpyrazine additive is 1,1'-(2,5-pyrazinediyl)bis-1-propanone.

5. A smoking composition comprising an admixture of (1) combustible filler selected from natural tobacco, reconstituted tobacco and tobacco substitutes, and (2) between about 0.0001-5 weight percent, based on the total weight of filler, of a 2,5-diacylpyrazine additive corresponding to the formula:

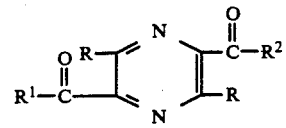

where R is hydrogen or an alkyl radical containing between about 1-4 carbon atoms; and $R^1$ and $R^2$ are alkyl radicals containing between about 1-10 carbon atoms, and $R^1$ and $R^2$ are different alkyl groups.

6. A smoking composition in accordance with claim 5 wherein the 2,5-diacylpyrazine additive is 1-[3,6-dimethyl-5-(1-propanoyl)-2-pyrazinyl]-3-methyl-1-butanone.

7. A smoking composition in accordance with claim 5 wherein the 2,5-diacylpyrazine additive is 1-[5-(ethanoyl)-2-pyrazinyl]-2,2-dimethyl-1-propanone.

8. A smoking composition in accordance with claim 5 wherein the 2,5-diacylpyrazine additive is 1-[5-(1-propanoyl)-2-pyrazinyl]-2-methyl-1-propanone.

9. A method of preparing a smoking composition which is adapted to impart flavor and aroma to mainstream and sidestream smoke under smoking conditions, which method comprises incorporating into natural tobacco, reconstituted tobacco or tobacco substitute between about 0.0001-5 weight percent, based on composition weight, of a 2,5-diacylpyrazine additive corresponding to the formula:

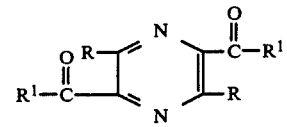

where R is hydrogen or an alkyl radical containing between about 1-4 carbon atoms; and $R^1$ is an alkyl radical containing between about 1-10 carbon atoms.

* * * * *